United States Patent [19]

Anderson et al.

[11] Patent Number: 5,430,813
[45] Date of Patent: Jul. 4, 1995

[54] MODE-MATCHED, COMBINATION TAPER FIBER OPTIC PROBE

[75] Inventors: George P. Anderson, Seabrook; Joel Golden, Ft. Washington, both of Md.

[73] Assignee: The United States of America as represented by the Secretary of the Navy, Washington, D.C.

[21] Appl. No.: 176,572

[22] Filed: Dec. 30, 1993

[51] Int. Cl.⁶ .............................................. G02B 6/14
[52] U.S. Cl. ...................................... 385/12; 385/28; 385/30; 385/43
[58] Field of Search ...................... 385/12, 28, 30, 31, 385/36, 43

[56] References Cited

U.S. PATENT DOCUMENTS

| | | | |
|---|---|---|---|
| 4,413,879 | 11/1983 | Berthold, III et al. | 385/43 X |
| 4,447,546 | 5/1984 | Hirschfeld | 436/527 |
| 4,654,532 | 3/1987 | Hirschfeld | 250/458.1 |
| 4,678,267 | 7/1987 | Burns et al. | 385/43 |
| 4,909,990 | 3/1990 | Block et al. | 422/82.11 |
| 4,991,926 | 2/1991 | Pavlath | 385/43 X |
| 5,061,857 | 10/1991 | Thompson et al. | 250/458.1 |
| 5,101,457 | 3/1992 | Blonder et al. | 385/33 |

OTHER PUBLICATIONS

Kronick et al., "A New Immunoassay Based on Fluorescence Excitation by Internal Reflection Spectroscopy," 8 Journal of Immunological Methods, pp. 235–239 (1975) (no month available).
Shriver-Lake et al., "The effect of Tapering the Optical Fiber on Evanscent Wave Measurements", 25 Analytical Letters 7, pp. 1183–1199 (1992) (no month available).
Golden et al., "Fluorometer and Tapered Fiber Optic Probe for Sensing in the Evanescent Wave," 31 Optical Engineering No. 7, pp. 1458–1462 (Jul. 1992).
G. P. Anderson, J. P. Golden and F. S. Ligler," A Fiber Optic Biosensor: Combination Tapered Fibers Designed for Improved Signal Acquisition," 8 Biosensors & Bioelectronics, pp. 249–256 (1993) (no month available).
Golden et al., "Ray Tracing Determination of Evanescent Wave Penetration Depth in Tapered Fiber Optic Probes," Reprinted from Chemical, Biochemical and Environmental Fiber Sensors IV in 1796 SPIE Proceedings Series, pp. 9–11 (Meeting 8–9 Sep. 1992 in Boston, Mass.; published Apr. 1993).
Golden et al., "An Evanescent Wave Fiber Optic Biosensor: Challenges for Real World Sensing," Reprinted from Chemical, Biochemical and Environmental Fiber Sensors IV in 1796 SPIE Proceedings Series, pp. 2–8 (Meeting 8–9 Sep. 1992, in Boston, Mass.; published Apr. 1993).
Thompson et al., "Sensitivity Enhancement for Evanescent Wave-Excited Fiber Optic Fluorescence Sensors," Reprinted from Time Resolved Laser Spectroscopy in Biochemistry II, 1204 SPIE Proceeding Series, pp. 35–41 (1990).

Primary Examiner—Frank Gonzalez
Attorney, Agent, or Firm—Thomas E. McDonnell; Ajay S. Pathak

[57] ABSTRACT

A combination tapered V number matching optical fiber probe is disclosed. The combination taper consists of a first short tapered section along the unclad, distal end of an optical fiber. The first short tapered section has a taper angle steeper than the taper angle of the second tapered section also along the unclad, most distal end of the optical fiber. The first short tapered section is adjacent to and proximal to the second tapered section. Proximal to the unclad, combination tapered section of the optical fiber is the cladded portion of the optical fiber. The cladding surrounds the core of the fiber. The optical fiber is used in conjunction with, for example, fluorescence assays as described herein.

20 Claims, 4 Drawing Sheets

MODE-MATCHED, COMBINATION TAPER FIBER OPTIC PROBE

BACKGROUND OF THE INVENTION

1. Field of the Invention

The present invention relates generally to waveguide-binding sensors for use in fluorescence assays, and, more particularly, to highly sensitive fiber-optic waveguide-binding sensors that remotely sense fluorescence radiation during assays in liquid solutions.

2. Description of the Related Art

The evanescent wave portion of an electromagnetic field produced by light propagating through an optical waveguide characteristically penetrates a few hundred nanometers into the medium surrounding the optical waveguide. This evanescent wave can excite fluorescent molecules, e.g., fluorophores, to fluoresce when they are bound by molecules near the optical waveguide surface. The application of this phenomenon to an immunoassay sensor, wherein the biological recognition (binding) of an antigen by antibodies attached to the waveguide surface with concomitant displacement of fluorescent-labeled antigen is measured as a change in fluorescence, was first disclosed in *A New Immunoassay Based on Fluorescence Excitation by Internal Reflection Spectroscopy* by Kronick and Little, 8 JOURNAL OF IMMUNOLOGICAL METHODS, p. 235 (1975), incorporated by reference herein in its entirety and for all purposes.

The use of optical fibers as a special class of waveguides for immunoassay sensors is also known. For example, U.S. Pat. No. 4,447,546, incorporated by reference herein in its entirety and for all purposes, discloses the use of optical fibers as waveguides which capture and conduct fluorescence radiation emitted by molecules near the optical fiber surfaces. However, conventional waveguide-binding sensors for use with assays of aqueous fluids have demonstrated inadequate sensitivity. Specifically, poor sensor performance is attributed at least in part to the small size of the sample being analyzed, typically, one or several monolayers in depth and the small surface area of the optical waveguide. These factors limit the number of fluorophores which may be excited. More serious sensor performance degradation is attributable to the effects of a weak evanescent wave which fails to excite enough fluorophores to produce detectable levels of fluorescence and inadequate coupling of the fluorescence into the waveguide for subsequent detection.

Increasing the strength of the evanescent wave penetrating into a fluid sample to be assayed increases the amount of fluorescence, thereby, increasing sensor sensitivity. Each mode (low and high order) propagating in the fiber has a portion of its power in the evanescent wave. Higher order modes have a larger percentage of their power in the evanescent wave and so make a larger contribution to power in the evanescent wave. However, these higher order modes are weakly guided, lossy, and can easily leak at a discontinuity or a bending point along the waveguide.

The use of tapered optical fibers to increase the sensitivity of fiber-optic assay systems is known. For example, U.S. Pat. Nos. 4,654,532 and 4,909,990, both incorporated by reference herein in their entirety and for all purposes, disclose the use of optical fibers as sensors used in conjunction with assays. In U.S. Pat. No. 4,654,532, an unclad, tapered optical fiber that is completely isolated from the sample fluid.

The introduction of a tapered section of the optical waveguide, however, fails to address certain important issues central to the sensitivity of these sensors, especially in remote sensing applications. In particular, the higher order modes propagating in the section of the waveguide where the fluorophores are found (the distal end) contribute the most to power in the evanescent wave and comprise the majority of the fluorescence coupled back into the fiber. These higher order modes typically propagate with greater loss than lower order modes.

For an incident beam of light of wavelength $\lambda$ traveling within a cladded core and intersecting the edge of a cladded core at the core and cladding boundary at an incident angle $\theta$ (measured from the normal of the reflecting edge) wherein the core has an index of refraction of $n_{core}$ and the cladding has an index of refraction of $n_{cladding}$, the thickness $d_p$ of the evanescent wave region contiguous and along the outer edge of the core penetrating into the cladding is given by the formula:

$$d_p = \frac{\lambda}{2\pi \sqrt{n_{core}^2 \sin^2\theta - n_{cladding}^2}}$$

If a portion of an optical fiber is unclad (i.e. the cladding is removed) and the bare core is surrounded by a solution having an index of refraction of $n_{solution}$, then, for an incident beam of light of wavelength $\lambda$ traveling within an uncladded core and intersecting the edge of the uncladded core at the core and solution boundary at an incident angle $\zeta$ (measured from the normal of the reflecting edge) wherein the core has an index of refraction of $n_{core}$ and the solution has an index of refraction of $n_{solution}$, the thickness $d_p$ of the evanescent wave region contiguous and along the outer edge of the core penetrating into the solution is given by the formula:

$$d_p = \frac{\lambda}{2\pi \sqrt{n_{core}^2 \sin^2\theta - n_{solution}^2}}.$$

Typically, the evanescent wave region has a thickness $d_p$ of between about 50-500 nm depending in part on the angle of incidence $\theta$ as described by the equations above. Fluorescence radiation excited within the evanescent wave region coupled into the core propagates in higher-order modes and is susceptible to losses due to microbending and V-number mismatch along the optical fiber.

U.S. Pat. No. 5,061,857, to Thompson et al., entitled Waveguide-Binding Sensor for Use With Assays, filed Nov. 9, 1990 and issued Oct. 29, 1991 (the entirety of which is incorporated by reference herein for all purposes) addresses concerns about poor V-number matching and the loss of poorly guided fluorescence radiation along the length of the optical fiber. The probe is inwardly tapered from the proximal to the distal end at an angle such that the incident light beam of light traveling through the fiber does not exceed the critical angle measured from the normal of the reflecting edge to the incident beam of light. Thus, total internal reflection (TIR) of the incident beam of light traveling within the optical fiber is maintained. The fiber may also be variably doped along its surface to similarly change the V-number along the length of the fiber. Fluorescence coupled in from radii above the V-number matching radius is lossy due to the V-number mismatch.

While the approach described in U.S. Pat. No. 5,061,857 improves over the prior art, it still results in significant losses. Most of the signal in this type of fiber optic sensor is generated at the tip. If the tip is damaged, the entire probe is ruined. Also, a significant length of the tapered portion is above the V-number matching radius. Thus, most of the signal from this V-number mis-matched portion is lost.

SUMMARY OF THE INVENTION

It is an object of the present invention to improve the sensitivity of fiber optic probes used in fluorescence assays.

It is another object of the present invention to enhance the power of excitation radiation within the evanescent wave region along the length of the sensing section of a fiber optic probe.

It is a further object of the present invention to propagate radiation, in fiber optic probes, from lower order modes of excitation radiation to higher order modes of excitation radiation with minimal loss, while maximizing the effective sensing area of the fiber optic probe.

These and other objects are achieved by a fiber optic probe having a sensing, distal end with a first inwardly tapered section and a second inwardly tapered section distal to the first inwardly tapered section. The first inwardly tapered section is more severely tapered, and extends for a shorter length than the second inwardly tapered section. The first inwardly tapered section tapers from a radius greater than the V-number matching radius down to the V-number matching radius, at the intersection of the first inwardly tapered section with the second inwardly tapered section. Along the first inwardly tapered section, the angle of inward taper may be maximized, such that the critical angle, in accordance with Snell's law, measured from the normal of the reflecting edge to the incident beam of light is not exceeded. Thus, total internal reflection (TIR) of the incident beam of light traveling within the optical fiber is maintained. In the second inwardly tapered section, the radius of the probe remains at or below the V-number matching radius. The angle of inward taper in the second inwardly tapered section is typically just that which is sufficient to enhance the concentration of the excitation light in the evanescent wave region.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENT(S)

Figure 1:
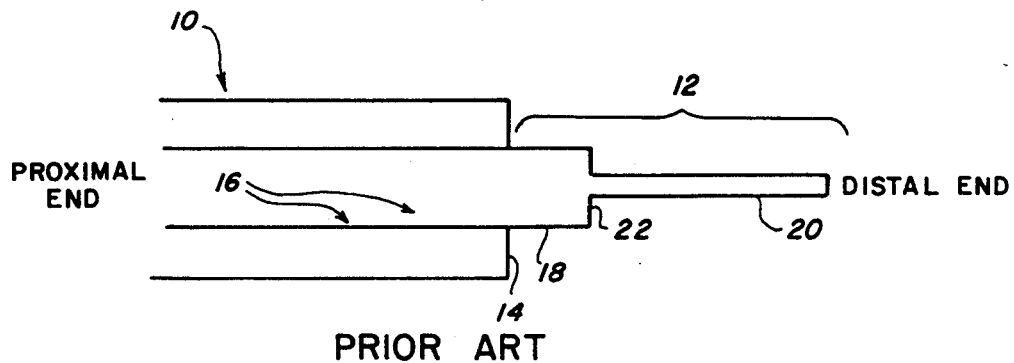
FIG. 1 is a plan view of one prior art embodiment of a fiber optic probe.

As shown in FIG. 1, prior art fiber optic probe 10 includes a distal end portion 12. At distal end portion 12, cladding 14 has been removed to expose the surface of the fiber core 16. Just distal to the end of the cladding, the radius of the fiber core abruptly changes from one that is above the V-number matching radius (in section 18) to one that is at or below the V-number matching radius (in section 20). Section 20, which is at or below the V-number matching radius, is the sensing portion of fiber optic probe 10.

The abrupt change in radius between sections 18 and 21) causes light to escape through flat surface 22 where sections 18 and 21) meet, reducing the radiation energy transmitted to the sensing portion. In addition, higher order modes of radiation are absorbed or scattered along the surface of sensing portion 20.

Figure 2:
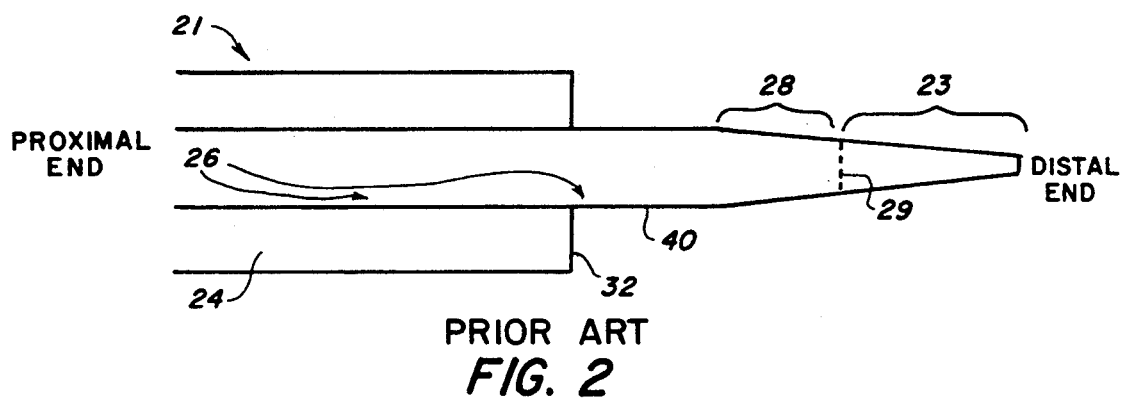
FIG. 2 is a plan view of another prior art embodiment of a fiber optic probe.

FIG. 2 shows yet another prior art fiber optic probe 21. At distal end section 40, cladding 24 has been removed to expose the surface of the fiber core 26. Just distal to the end of cladding 24, the radius of the fiber core gradually changes, at a constant rate, from one that is above the V-number matching radius (along section 28) to one that is at the V-number matching radius (along line 29, the intersection of sections 28 and 23) to below the V-number matching radius (along section 23). Section 23 is now known to be the effective sensing portion of fiber optic probe 21. Because section 28 is above the V-number matching radius, it couples inefficiently. Thus, a significant portion of the fluorescent signal is still lost in optical probes employing a continuous taper. Additionally, most of the fluorescent signal is generated at the very distal end (section 23) of this probe. If this end of the probe is broken or otherwise impaired, the entire probe must be discarded.

Figure 3:
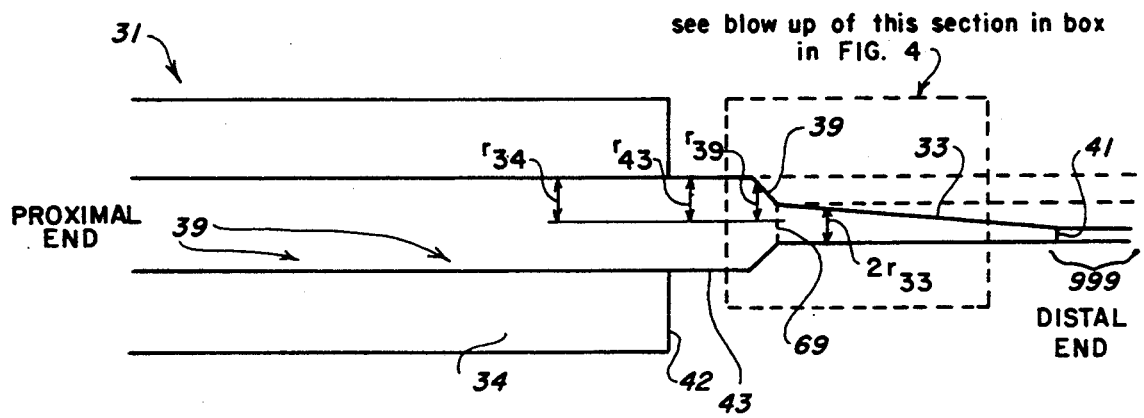
FIG. 3 is a plan view of a fiber optic probe according to the present invention.

FIG. 3 shows a fiber optic probe 31 according to the present invention. Along distal end portion 39 and 33, cladding 34 has been removed to expose the surface of the fiber core 36. Just distal to the end of cladding 36, the radius of the fiber core in section 39 continuously tapers down to the V-number matching radius over a short distance. The radius of the section 33 tapers down slightly in the direction of tip 41. At the intersection of sections 33 and 39 at line 69, the radius of the probe ($r_{39} = r_{33} = r_{match}$) equals the V-number matching radius $r_{match}$.

Figure 8:
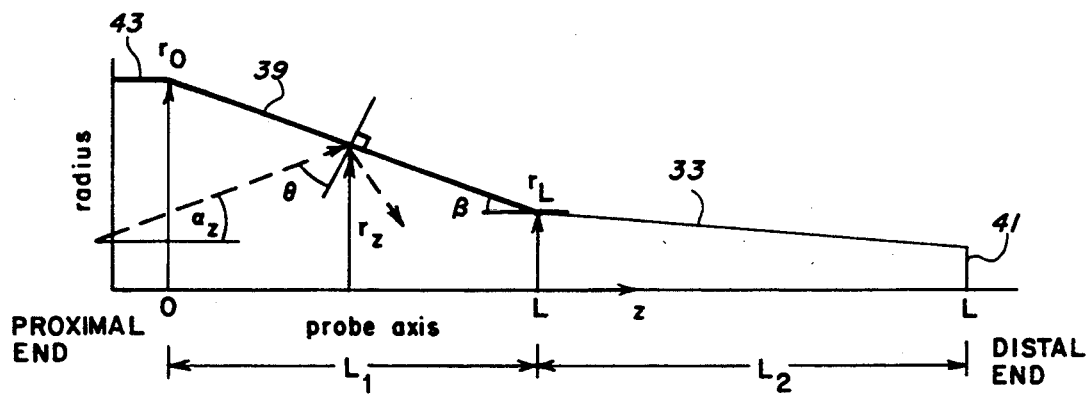
FIG. 8 is a schematic of a beam of incident light traveling through the distal, unclad, combination tapered end of the optical fiber.

Referring to FIG. 8, the symbols within the figure represent the following:
(1) $r_0$ is the radius of the unclad optical fiber at any point along the fiber that is proximal to the first tapered section 39;
(2) $a_0$ is the angle of the incident beam of light measured with respect to the longitudinal axis of the optical fiber at any point along the unclad, optical fiber that is proximal to the first tapered section 39;

(3) $r_z$ is the radius of the unclad optical fiber at any point along the tapered, unclad, optical fiber within first and second tapered sections 39 and 33, respectively, where the incident beam of light intersects the reflecting edge;

(4) $a_z$ is the angle of the incident beam of light measured with respect to the longitudinal axis of the optical fiber at any point along the tapered, unclad, optical fiber within first and second tapered sections 39 and 33, respectively;

(5) $\theta$ is the angle of incidence of the beam of light (measured from the normal of the reflecting surface) traveling within tapered sections 39 or 33 at any point along the tapered, unclad, optical fiber within first and second tapered sections 39 and 33, respectively;

(6) $\beta$ is the angle of inward taper of either tapered section 39 or 33 measured with respect to the longitudinal axis of the optical fiber at any point along the tapered, unclad, optical fiber within first and second tapered sections 39 and 33, respectively;

(7) $L_1$ is the longitudinal length of the first tapered section 39; and (8) $L_2$ is the longitudinal length of the second tapered section 33, all as shown in FIG. 8.

The following equations describe the relationships between the variables described in (1)–(8) above and as shown in FIG. 8:

$$r_0 \sin(\alpha_0) = r_z \sin(\alpha_z),$$

$$\tan(\alpha_z) = r_z/L_1, \text{ and}$$

$$L_1 = r_z/(\tan(90 - \theta - \beta)).$$

Typically, the longitudinal length, $L_1$, of the first tapered section 39 is between about 0.1%–30% of the longitudinal length, $L_2$, of the second tapered section 33. Preferably, $L_1$ is between about 1%–20% of the length $L_2$. More preferably, $L_1$ is between about 2%–15% of the length $L_2$. Most preferably, $L_1$ is between about 5%–12% of the length $L_2$. The taper angle $B_2$ in section 33 should always be more gradual than the taper angle $B_1$ in section 39 (See FIG. 4).

To maintain total internal reflection, section 39 should be tapered inwardly from the proximal to the distal end at a taper angle $B_1$ such that an incident beam of light traveling through the fiber does not fall below the critical angle measured from the normal of the reflecting outer edge of section 39 to the incident beam of light. The incident beam of light is the excitation light traveling in the net direction from the proximal end of the fiber 31 towards its distal end. Because section 39 does not efficiently couple fluorescent signals generated at its surface, its length $L_1$ is preferably minimized.

The equation for calculating the number of modes ($V^2/2$) that can be propagated at any given point along the cladded fiber (FIG. 3; i.e. core 36 surrounded by cladding 34) is given by the following equation:

$$V_{34} = \frac{2\pi r_{34}}{\lambda} \sqrt{n_{core}^2 - n_{cladding}^2}$$

where (1) $V_{34}$ is the determines the number of modes that can be propagated along the cladded optical fiber at the point on the fiber wherein its radius is $r_{34}$ from the center of the optical fiber to the outermost core surface;

(2) $n_{core}$ is the index of refraction of the core of the fiber;

(3) $n_{cladding}$ is the index of refraction of the cladding;

(4) $\lambda$ is the wavelength of the fluorescent signal captured by the fiber core at its distal, non-cladded end (sections 39 and 33) i.e. the fluorescent signal emanating from the fluorophore in the evanescent wave portion near the distal end (section 33) of the unclad fiber.

Note that at the distal, unclad end of the fiber (sections 43, 39 and 33), the value of $n_{cladding}$ is substituted with the value of $n_{solution}$ which is the index of refraction of the solution into which the distal, sensing end of the fiber is immersed. In addition, at the unclad, distal end of the fiber (sections 43, 39 and 33), the values of $r_{43}$, $r_{39}$ and $r_{33}$ are used instead of $r_{34}$ when calculating the V-number in sections 43, 39 and 33, respectively. Note that $r_{43}$ is the radius of the unclad fiber along section 43, $r_{39}$ is the radius of the unclad, tapered fiber along section 39 and $r_{33}$ is the radius of the unclad, tapered fiber along section 33. Thus, the number of modes ($V^2/2$) that can be propagated at any given point along the unclad fiber (sections 43, 39 and 33) can be calculated using the following equations:

$$V_{43} = \frac{2\pi r_{43}}{\lambda} \sqrt{n_{core}^2 - n_{soluiton}^2}$$

$$V_{39} = \frac{2\pi r_{39}}{\lambda} \sqrt{n_{core}^2 - n_{solution}^2} \text{ and}$$

$$V_{33} = \frac{2\pi r_{33}}{\lambda} \sqrt{n_{core}^2 - n_{solution}^2}$$

For example, the number of modes within section 39 would be $(V_{39})^2/2$.

Maximum efficiency in the propagation of the captured fluorescent signal from the distal, unclad sections of the optical fiber (sections 43, 39 and 33) into and along the proximal, cladded section (section 34) of the fiber is accomplished when $V_{34} \geq V_{43} \geq V_{39} \geq V_{33}$. Generally, without tapering, $V_{34}$ would be less than $V_{33}$ ($V_{34} < V_{33}$) and $V_{39}$ ($V_{34} < V_{39}$). Therefore, it is necessary to reduce the value of $V_{33}$ such that $V_{34} \geq V_{33}$. One way to reduce the value of $V_{33}$ is to reduce the radius from $r_{34}$ ($r_{34} = r_{43}$) to $r_{33}$ such that $V_{34} \geq V_{33}$. In order to maximize the length $L_2$ of the unclad, distal portion 33 of the optical fiber and to have $V_{34} \geq V_{33}$, a first short tapered section 39 is used to reduce the radius from $r_{39}$ where $V_{34} < V_{39}$ to $r_{39}$ where $V_{34} = V_{39}$ at the distal, unclad end of the first short tapered section 39 at line 69. Here a first short tapered section 39 is used instead of a 90 degree step down to a value of $r_{39}$ where $V_{34} = V_{39}$ because using a first short tapered section 39 avoids the problem of falling below the critical angle by an incident beam of excitation radiation at the 90 degree step. The critical angle is measured from the normal drawn perpendicular to the reflecting, unclad edge to the incident excitation beam. Use of a step down instead of a first short taper down to $r_{39} = R_{match}$ (distal end of section 39) at line 69 where $V_{34} = V_{39}$ causes the angle of incidence to fall below the critical angle at the step 22 and results in a loss of the excitation light and further causes unwanted excitation of the unbound fluorophore in the bulk solution.

Thus, section 39 is tapered inwardly by gradually reducing $r_{39}$ from a value where $V_{34}<V_{39}$ to a matching radius ($r_{39}=r_{match}$) where $V_{34}=V_{39}$ at line 69. The angle $B_1$ of taper is inward toward the center of the unclad fiber along the first short tapered section 39 proceeding toward the distal, unclad end of the fiber. The taper angle $B_1$ along the first short tapered section 39 is typically between about 0.01–30 degrees, preferably between about 0.05–25 degrees, more preferably between about 0.1–10 degrees and most preferably between about 0.2–5 degrees measured from the outer untapered surface 43 of the unclad fiber (or a line parallel to the untapered, unclad surface 43) toward the center of the fiber along the taper outer edge of the unclad fiber, the taper angle $B_1$ opening toward the distal, unclad end of the fiber.

Along the distal, unclad end of the fiber, a second tapered section 33 begins at the point at the distal end of the first short tapered section 39 at line 69 where $r_{39}$ is such that $V_{34}=V_{39}$. The second tapered section 33 is tapered inwardly and the taper angle $B_2$ opens toward the distal, unclad end of the fiber. The second taper angle $B_2$ is shallower than the angle $B_1$ of the first short tapered section 39 which first short tapered section 39 is located adjacent to the second tapered section 33 and which first short tapered section 39 is located proximal to the second tapered section 33. The value of $r_{33}$ located at the intersection of the most proximal end of the second tapered section 33 and the most distal end of the first short tapered section 39 at line 69 is equal to $r_{match}$ such that $V_{34}=V_{39}=V_{33}$ at line 69. The taper angle $B_2$ along the unclad portion of the optical fiber and along the second tapered section 33 opens toward the distal end of the optical fiber, as does the taper angle $B_1$ of the first short tapered section 39 discussed earlier. The radius $r_{33}$ equals $r_{39}$ which equals $r_{match}$ at the most proximal portion of the second tapered section 33. The radius $r_3$ is gradually reduced from a value of $r_{33}$ where $V_{39}=V_{33}$ at line 69 to a value of $r_{33}$ where $V_{39}>V_{33}$.

To maintain total internal reflection, section 33 should be tapered inwardly from the proximal to the distal end at a taper angle $B_2$ such that an incident beam of light traveling through the fiber does not fall below the critical angle measured from the normal of the reflecting outer edge of section 33 to the incident beam of light. The incident beam of light is the excitation light traveling in the net direction from the proximal end of the fiber 31 towards its distal end.

With the value of $V_{39}>V_{33}$ in the second tapered region 33, except at the boundary at line 69 between the second tapered, uncladded core section 33 and the first short tapered, uncladded core section 39 where $V_{39}=V_{33}$, the maximum amount of the incoming fluorescent signal captured from the fluorophore bound to molecules attached to the distal, uncladded second tapered section 33 core surface, is transmitted to the adjacent first short tapered section 39 uncladded core. Proximal to the boundary line 69, $V_{39}>V_{33}$. The incoming signal traveling into the first short tapered section 39 uncladded core from the second tapered section 33 uncladded core is further transmitted into the cladded, untapered section of the fiber where $V_{34}<V_{39}$ except at line 69 where $V_{34}=V_{39}=V_{33}$. Except at line 69 where $V_{34}=V_{39}=V_{33}$, the tapering in sections 39 and 33 is done such that the condition $V_{43}>V_{39}>V_{33}$ is also met.

Having described the invention, the following examples are given to illustrate specific applications of the invention, including the best mode now known to perform the invention. These specific examples are not intended to limit the scope of the invention described in this application.

EXAMPLES

Fluorimeter Configuration

Figure 5:
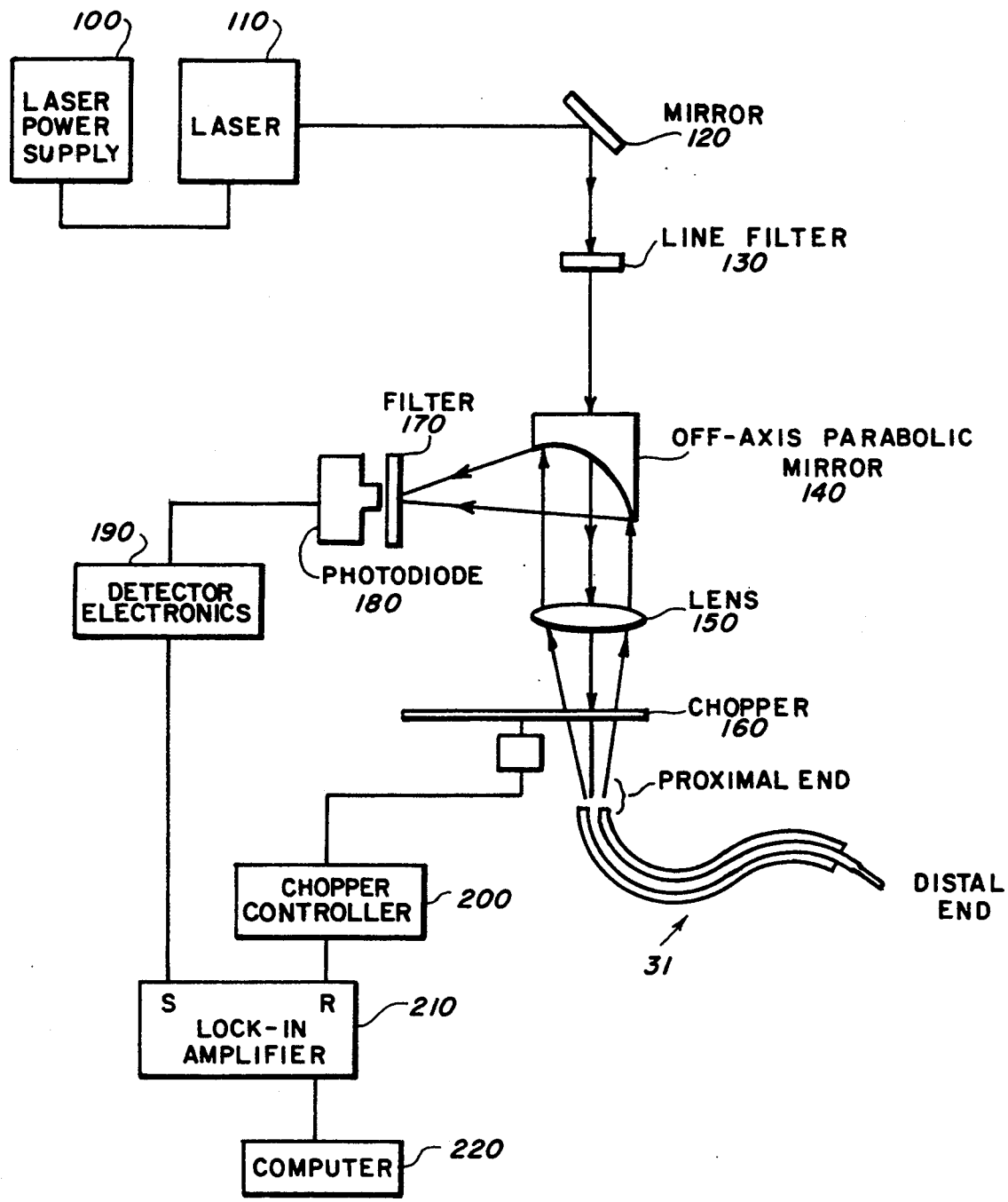
FIG. 5 is a schematic layout of a typical fiber optic probe apparatus according to the present invention.

The components used in conjunction with the biosensor were selected to minimize noise and, thus, improve signal discrimination. A schematic of the fiber optic fluorimeter utilized is shown in FIG. 5. The detection optics were encased in a light-proof metal enclosure to reduce the effects of ambient light and electromagnetic influence on the detector circuitry. Table 1 shows the power drop across each component. The numbers represent the power drop at 514 nm measured across the fiber optic fluorometer components listed in Table 1 below.

TABLE 1

| Component | Power Drop (dB) |
| --- | --- |
| Mirror | 0.02 |
| Line Filter | 1.55 |
| Parabolic Mirror | 0.32 |
| Objective Lens | 0.49 |
| Chopper | 3.01 |
| Liquid & 3-66 Filters | 34.78 |
| KV550 Filter | 35.60 |

Key components shown in FIG. 5 include optics for launching and collecting the light, kinematic mounts (not shown), the off-axis parabolic mirror and the emission filter.

A laser light source was selected for its moderate power, stability, narrow excitation bandwidth and efficient light coupling into the fiber 31. The exemplary rhodamine-based fluorescent labels used with the sensor were excited at 514 nm and emit in the 570($\pm$50 nm) nm range where there is little intrinsic fluorescence in most clinical and environmental samples. A 514 nm laser beam from an air-cooled 50-mW argon ion laser 110 (Omnichrome 532, Chino, Calif.) was launched into the most proximal end of the cladded fiber. The laser 110 was adjusted to a 12-mW output to minimize bleaching of the fluorophores bound to the distal end of the optical fiber 31. The line filter (Melles Griot) 130 removed plasma lines from the laser source. The laser beam from laser 110, powered by laser power supply 100, was reflected by mirror 120 into the line filter 130. The laser beam passed through the line filter 130 and through an off-axis parabolic mirror (Melles Griot) 140. The laser beam was focused by a spherical lens (f/1, one inch focal length bioconvex lens; Newport Corporation) 150 onto the proximal end of the optical fiber 31 through chopper 160. The laser beam focused by the spherical lens 150 focused the light onto the fiber, filling only a small portion of the fiber's numerical aperture. Approximately, 8 degrees of the fiber's numerical aperture of 23 degrees were filled. This simple lens 150 proved easier to use than a microscope objective and provided ample room for the insertion of the chopper 160 between it and the proximal end of the optical fiber 31. Positioning the chopper (Stanford Research Systems) 160 near the proximal end of the fiber instead of at the laser 110 reduced the background noise from scattered excitation light. See Table 2 below.

TABLE 2

| Device Configuration | Signal (mV) | Noise (mV) | S/N[b] | $N_1/N_0$[c] |
|---|---|---|---|---|
| NRL Device w/KV550 (Std) | 0.99 | 0.095 ($N_0$) | 10.42 | 1.00 |
| Chopper Placed by Laser | 1.13 | 0.13 | 8.69 | 1.36 |
| Minus Excitation Filter | 2.08 | 0.59 | 3.53 | 6.21 |
| Liquid→3-66 filter[a] | 0.93 | 0.20 | 4.65 | 2.10 |
| 3-66→Liquid filter | 3.58 | 2.71 | 1.32 | 29 |
| 3-66 filter (only) | 7.20 | 6.38 | 1.13 | 67 |
| Liquid filter (only) | 323 | 322 | 1.003 | 3389 |

[a]→indicates the light path toward the photodiode
[b]The signal (S) was obtained by placing fluorescent paper a sufficient distance from the end of a cleaved fiber to produce a reading of ~ 1mV with the standard configuration. The background noise level (N) was the voltage reading without the fluorescent paper.
[c]$N_1/N_0$ is the background level produced by the configuration under test divided by that of the standard configuration, NRL Device w/KV550.

The chopper 160 and photodiode (EG&G Judson) 180 were connected to a lock-in amplifier (LIA, Stanford Research Systems, Sunnyvale, Calif.) 210. The photodiode 180 was selected rather than a photomultiplier tube because of low cost, reliability and compatibility with the lock-in amplifier 210. The chopper 160 was interfaced to the lock-in amplifier (LIA) 210 anal computer 220 for phase sensitive detection via chopper controller 220. The collected fluorescence signal from the distal end of the optical fiber 31 traveled the reverse path to the parabolic mirror 140 where it was refocused through a longpass filter (KV550) 170 onto a silicon photodiode 180 which was also connected to the LIA 210.

All components were mounted in the device (See schematic FIG. 5) with detachable kinematic mounts (not shown). The high degree of reliability with which kinematic mounts can be removed and reinstalled permitted rapid setup of the optics upon relocation. The fiber connectors (not shown) were held in an x-y adjustable mount (not shown) to allow for precise positioning of the fiber in the laser beam. The off-axis parabolic mirror 140, lens 150 and photodiode 180 were also mounted using x-y or x-y-z adjustable mounts (not shown) to permit rapid alignment.

A design improvement maintained in this device was the perforated off-axis parabolic mirror 140. The central perforation passes the laser excitation while the mirror 140 focuses the fluorescence signal in a direction orthogonal to the laser beam and onto the photodiode 180. The use of this mirror 140 was found to improve the signal-to-noise ratio (SNR) not only by providing an efficient collecting surface for returning fluorescent light, but also by assisting in the removal of long wavelength plasma lines, which are poorly collimated in comparison to the laser beam. In addition, the parabolic mirror 140 added to the device's versatility, because collection of various fluorescent wavelengths can be accomplished without replacement of an expensive dichroic mirror. The focusing lens 150 that served to launch the laser light into the fiber 31 had a numerical aperture greater than that of the cladded fiber 31. Thus, it also served to collimate all of the returning fluorescence onto the parabolic mirror 140.

The parabolic mirror 140 focused the fluorescence signal onto a photodiode 180 through a KV550 longpass filter (Schott-Glass) 170 that blocked any stray excitation light. The KV550 filter 170 has a lower wavelength absorption cutoff than the Corning 3-66 filter (alternative filter 170) previously used, thus permitting more fluorescence signal to reach the photodiode. The change to the KV550 filter also eliminated the need for the liquid filter (5% $K_2Cr_2O_7$), which was necessary to reduce the fluorescence generated by stray light hitting the Corning 3-66 filter (alternative filter 170). Fluorescence from the 3-66 filter is demonstrated by the 13-fold increase in background noise upon switching the order of the liquid and 3-66 filters in the light path (Table 2, supra). See L. C. Shriver-Lake, G. P. Anderson, J. P. Golden and F. S. Ligler, *The effect of Tapering the Optical Fiber on Evanescent Wave Measurements* 25 ANALYTICAL LETTERS 7, pp. 1183–1199 (1992), incorporated by reference herein in its entirety and for all purposes. See J. P. Golden, L. C. Shriver-Lake, G. P. Anderson, R. B. Thompson and F. S. Ligler, *Fluorometer and Tapered Fiber Optic Probe for Sensing in the Evanescent Wave* 31 OPTICAL ENGINEERING No. 7, pp. 1458–1462 (July 1992), incorporated by reference herein in its entirety and for all purposes. See G. P. Anderson, J. P. Golden and F. S. Ligler, *A Fiber Optic Biosensor: Combination Tapered Fibers Designed for Improved Signal Acquisition,* 8 BIOSENSORS & BIOELECTRONICS, pp. 249–256 (1993), incorporated by reference herein in its entirety and for all purposes. See J. P. Golden, S. Y. Rabbany and G. P. Anderson, *Ray Tracing Determination of Evanescent Wave Penetration Depth in Tapered Fiber Optic Probes,* Reprinted from CHEMICAL, BIOCHEMICAL AND ENVIRONMENTAL FIBER SENSORS IV in 1796 SPIE PROCEEDINGS SERIES, pp. 9–11 (Meeting 8–9 Sep. 1992 in Boston, Mass.; published April 1993), incorporated by reference herein in its entirety and for all purposes. See J. P. Golden, G. P. Anderson, R. A. Ogert, K. A. Breslin and F. S. Ligler, *An Evanescent Wave Fiber Optic Biosensor: Challenges for Real World Sensing,* Reprinted from CHEMICAL, BIOCHEMICAL AND ENVIRONMENTAL FIBER SENSORS IV in 1796 SPIE PROCEEDINGS SERIES, pp. 2–8 (Meeting 8–9 Sep. 1992 in Boston, Mass.; published April 1993), incorporated by reference herein in its entirety and for all purposes. See R. B. Thompson and L. Kondracki, *Sensitivity Enhancement for Evanescent Wave-Excited Fiber Optic Fluorescence Sensors,* Reprinted from TIME RESOLVED LASER SPECTROSCOPY IN BIOCHEMISTRY II, 1204 SPIE PROCEEDING SERIES, pp. 35–41 (1990), incorporated by reference herein in its entirety and for all purposes.

Optical Probe Preparation

The fiber optic probe 31 used in this biosensor was made from a length of step-index plastic clad silica optical fiber (200 μm diameter core, Quartz et Silice, Quartz Products, Tuckerton, Del.) 31 with a connector (not shown) on the proximal end to facilitate replacement and alignment. The distal end was modified to perform biochemical assays in the evanescent wave. Lengths up to 60-m have been successfully tested, but 1-m lengths were used for convenience. A metal SMA 905 connector (Amphenol Fiber Products, Lisle, Ill.) and a small ferrule connector (Aurora Optics Inc.) (both not shown) were tested. The metal SMA 905 connector was attached to the fiber core with non-fluorescing epoxy (Epoxy Technologies, Billerica, Mass.) and secured with a crimped metal sleeve and heat shrink tubing (both not shown). The fiber was cleaved on the proximal end of the connector (not shown) and polished using a Buehler FibrPol fiber-optic polisher (Buehler, Lake Bluff, Ill.). The proximal fiber face was polished for efficient launching of light into the fiber 31. Light reflecting off the polished SMA connector (not shown) toward the photodiode 180 was the source of significant background noise. The polished face of the SMA connector was roughened with acid etching using HCl:HNO$_3$ (3:1 vol:vol) and blackened or painted with flat black enamel paint to reduce the back reflection. This reduced the background signal measured when using the Corning 3-66 filter. However, the need for the painting step became unnecessary because the relatively nonfluorescent KV550 filter 170 yields low background levels for all of the connectors. See J. P. Golden, L. C. Shriver-Lake, G. P. Anderson, R. B. Thompson and F. S. Ligler, *Fluorometer and Tapered Fiber Optic Probe for Sensing in the Evanescent Wave* 31 OPTICAL ENGINEERING No. 7, pp. 1460 FIG. 2, (July 1992), incorporated by reference herein in its entirety and for all purposes. Use of the plastic ferrule connector was attractive because it is much smaller, lighter and less expensive than the SMA connector. The ferrule connector expedited connection of the optic probe 31 to the device (schematic of FIG. 5; plastic connector not shown).

At the distal end of the fiber 31, 12.5 cm of cladding was stripped away from the core by removal of the buffer (not shown) and cladding 34 with a razor blade. Residual cladding was removed by immersing this end of the optical fiber in concentrated hydrofluoric acid (HF) for 1 minute. This distal end portion of the fiber was the sensing region on which the detection molecules were immobilized. The sensing region was immersed in an aqueous sample that had an index of refraction less than that of the optical fiber cladding 34. The combination taper probe (i.e. the combination of a first short tapered section 39 and a second longer, shallower tapered section 33) was prepared by slowly immersing the declad distal end of the fiber into concentrated HF, using a computer controlled stepper motor.

For the combination taper probe, 2 cm of distal, unclad end of the fiber 31 was first lowered into the concentrated HF acid. For convenience, referring to FIG. 7, this 2 cm end is depicted as untapered section 999 (separate from section 33) which is used to glue the tee-connection 520 and the sample outlet 540 as shown. Then the distal, unclad end of the fiber 31 was lowered at a constant rate of about 0.53 cm/minute for the next 9 cm to create the gradually tapered second section 33. The final 1 cm of the combination tapered probe was lowered at a constant rate of about 0.045 cm/minute into to the concentrated HF acid. This relatively steep tapered section 39 was tapered from the original 100 $\mu$m radius (at $r_{43}$ along section 43) down to the V-number matching radius at line 69 of 63 $\mu$m. The taper dimensions were measured with a calibrated optical microscope. See G. P. Anderson, J. P. Golden and F. S. Ligler, *A Fiber Optic Biosensor: Combination Tapered Fibers Designed for Improved Signal Acquisition*, 8 BIOSENSORS & BIOELECTRONICS, pp. 250-251 and FIG. 1 at pp. 250 (1993), incorporated by reference herein in its entirety and for all purposes.

Model Immunoassay

Figure 4:
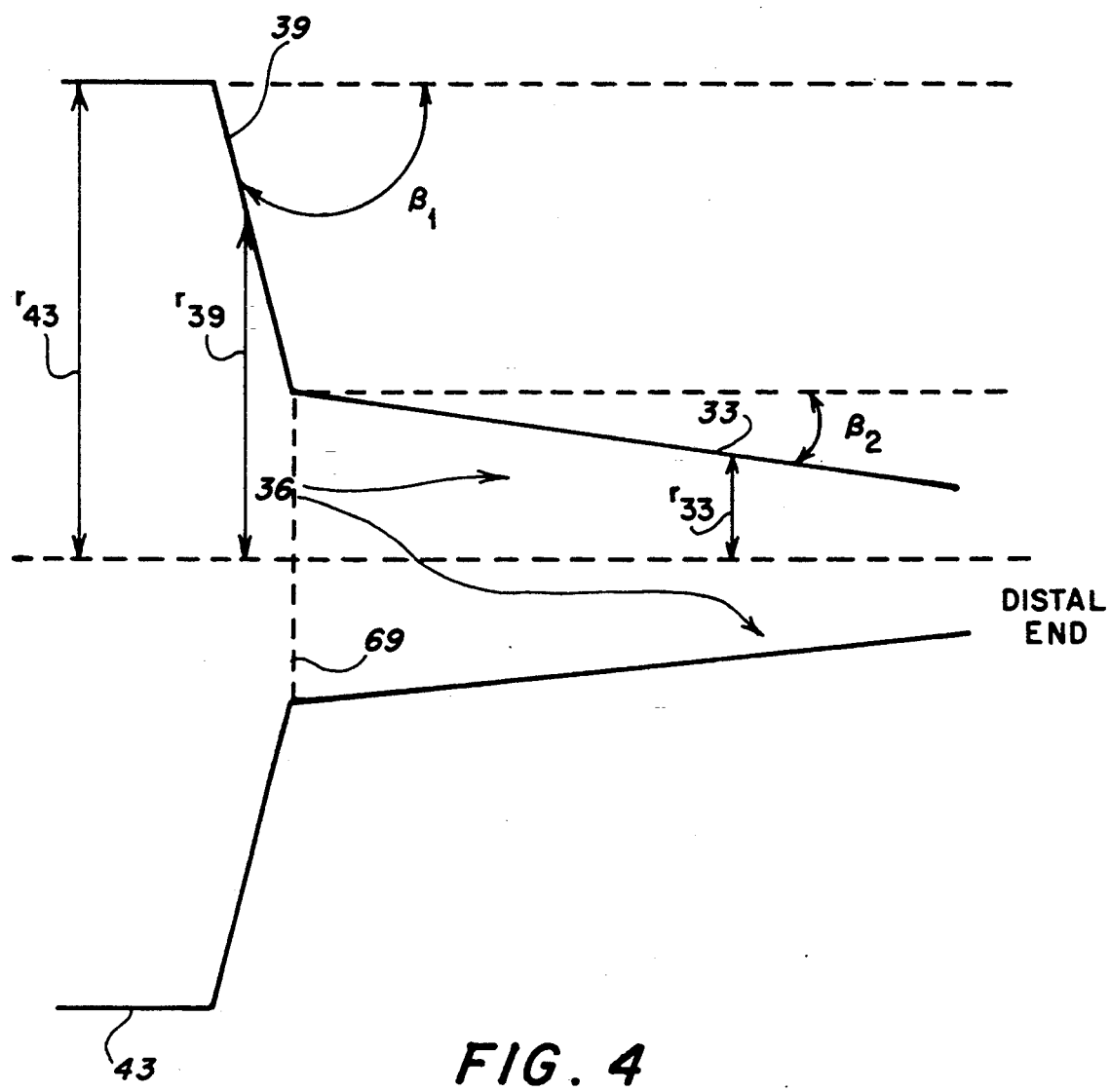
FIG. 4 is a plan view of the distal, unclad end of the fiber optic probe according to the present invention.
Figure 6:
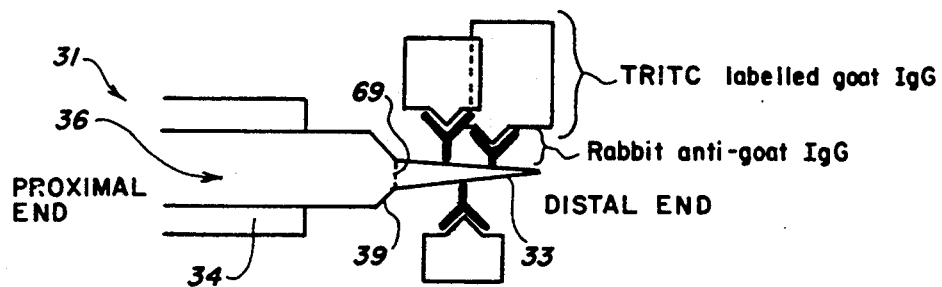
FIG. 6 is a schematic layout of the sensing distal end of the fiber optic probe having attached to it an antibody and a fluorescently labelled antigen attached to the antibody attached to the optical fiber.
Figure 7:
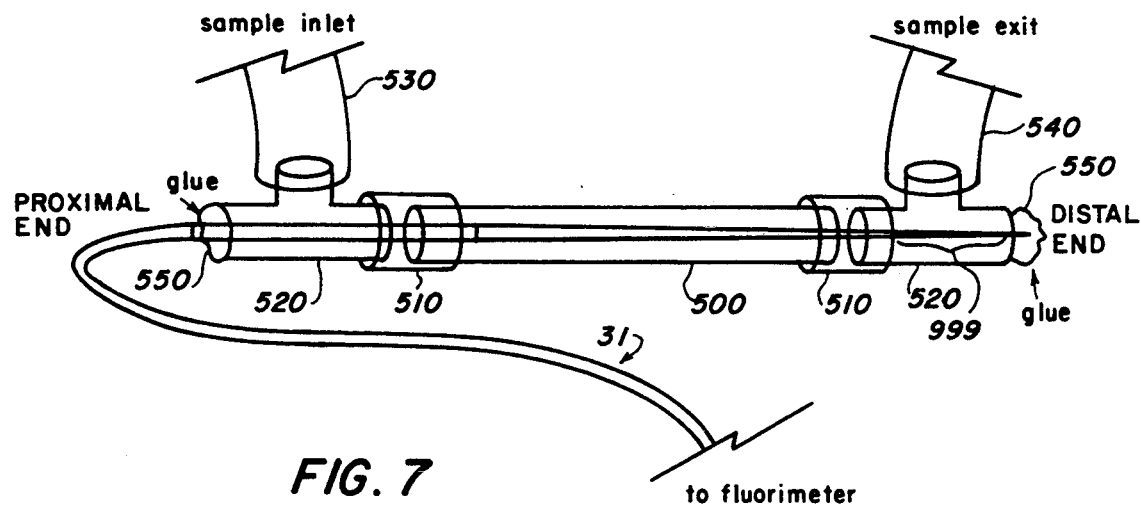
FIG. 7 is a schematic layout of the sensing distal end of the fiber optic probe held within a capillary tube having tee connections as shown. Note that the first and second tapered sections shown in FIGS. 3 and 4 are present but not shown.

To investigate the factors which affect the sensitivity and reproducibility of the system, a simple immunoassay was used. The assay was the binding of TRITC (tetramethyl rhodamine-5-isothiocyanate)-labelled goat IgG (Jackson Lab., West Grove, Penn.) 300 to rabbit anti-goat IgG (Jackson Lab., West Grove, Penn.) 310 attached to the surface of the uncladded, tapered fiber core 33. See FIG. 6. The entire uncladded combination taper fiber sensing region (sections 33 and 39) was sealed into a flow chamber constructed from a shortened 200 $\mu$l capillary tube 500 and tee connectors 510 & 520, having a total length of 13 cm. See FIG. 7. Note that the tapered sections 39 and 33 are not shown in FIG. 7 but are present as shown in FIGS. 3 and 4. The distal end of the fiber was glued outside the chamber, allowing only light from the evanescent wave to enter the fiber surrounded by the solution within the tee connection capillary. Both ends of the capillary tube were sealed with hot-melt glue 550, with the clad region of the fiber extending into the proximal portion of the apparatus. The sample to be tested was introduced over the distal end of the optical fiber 31 via sample inlet 530 and exited at sample outlet 540. Use of this capillary tube apparatus as shown in FIG. 7 allows one to test a given sample solution over the distal end of the optical fiber 31 and to wash the distal end of the fiber before introducing another sample solution through the sample inlet 530 and exited at sample outlet 540 in one continuous step. Signal return from the fiber was compared for various concentrations of TRITC-labelled goat IgG circulated over the fiber.

Signal acquisition along fiber length

After saturation of the binding capacity of the antibody-coated fiber (see FIG. 6; distal end of optical fiber 31 coated with antibody 310) with TRITC-labelled goat IgG 300, the fiber was removed from the capillary tube 500 and placed in phosphate buffered saline (PBS). With signal still being generated from the bound TRITC-labelled goat IgG, 1 cm sections of the fiber were removed sequentially from the distal end of the fiber and the signal was measured at each length. The fiber's distal end could remain in the PBS solution since there was no free fluorophore in solution. The combination taper (sections 39 and 33) fiber coupled a significant portion of its total signal along the entire length of the sensitized section (section 33).

Comparison of combination taper fibers

To select the optimal combination taper (sections 39 and 33) fiber, various tapers were tested. All had a short first tapered section 39 of about 1 cm length which rapidly tapered down to the V-number matching radius of 63 $\mu$m. Then each fiber had a longer section 33 of about 9 cm which tapered gradually down to either a 62 $\mu$m, 51 $\mu$m, 35 $\mu$m or 26 $\mu$m end radius (i.e. the $r_{33}$ at tip 41). These fibers were then tested in an immunoassay and compared to the signal recorded for a control coated with goat IgG which does not specifically bind to TRITC labelled goat IgG present in the bulk solution. No significant signal was detected from unbound material until the TRITC-labelled goat IgG's 300 concentration reached 33 nM with the control goat IgG coated combination taper. At 33 nM, the signal from the control fiber was less than 10% of the signal from the specific antibody-coated fibers. After these fibers were nearly saturated by incubating for 4 min. at 33 nM, they were washed briefly with PBS to ensure the signal was due only to surface-bound fluorescent molecules and the signal minus background was determined. It was revealed that while the signal rose only slightly as the fiber end radius was further tapered, the yield of signal (($\mu$V of signal)/(cm$^2$ of surface area on fiber)) per cm$^2$ increased significantly.

Further details of the immunoassay used are disclosed in the article by G. P. Anderson, J. P. Golden and F. S.

Ligler, *A Fiber Optic Biosensor: Combination Tapered Fibers Designed for Improved Signal Acquisition,* 8 BIOSENSORS & BIOELECTRONICS, pp. 249–256 (1993), incorporated by reference herein in its entirety and for all purposes.

What is claimed is:

1. A combination tapered sensing optical fiber, said optical fiber comprising:
   (a) a proximal section of the optical fiber having a core and a cladding, said cladding covering a first portion of said core, said first portion further having a first V-number;
   (b) a distal section of the optical fiber having an exposed core, said distal section further having:
      (1) a proximal first section and an adjacent distal second section wherein:
         (i) said proximal first section is tapered at a first angle, toward the center of said core of said distal section from a first radius having a second V-number higher than the first V-number down to a second radius having a third V-number equal to the first V-number;
         (ii) said distal second section is tapered at a second angle, shallower than said first angle, toward the center of said core of said distal section from said second radius having the third V-number equal to the first V-number.

2. The optical fiber of claim 1 wherein said proximal first section has a first longitudinal length and said distal second section has a second longitudinal length.

3. The optical fiber of claim 2 wherein said first longitudinal length is between about 0.1%–30% of said second longitudinal length.

4. The optical fiber of claim 2 wherein said first longitudinal length is between about 1%–20% of said second longitudinal length.

5. The optical fiber of claim 2 wherein said first longitudinal length is between about 2%–15% of said second longitudinal length.

6. The optical fiber of claim 2 wherein said first longitudinal length is between about 5%–12% of said second longitudinal length.

7. The optical fiber of claim 1 wherein said first angle is between about 0.01–30 degrees.

8. The optical fiber of claim 1 wherein said first angle is between about 0.05–15 degrees.

9. The optical fiber of claim 1 wherein said first angle is between about 0.1–10 degrees.

10. The optical fiber of claim 1 wherein said first angle is between about 0.2–5 degrees.

11. A combination tapered sensing optical fiber for use in fluorescence assays, said optical fiber comprising:
    (a) a proximal section of the optical fiber having a core and a cladding, said cladding covering a first portion of said core, said first portion further having a first V-number;
    (b) a distal section of the optical fiber having an exposed core, said distal section further having:
       (1) a proximal first section and an adjacent distal second section wherein:
          (i) said proximal first section is tapered at a first angle, toward the center of said core of said distal section from a first radius having a second V-number higher than the first V-number down to a second radius having a third V-number equal to the first V-number;
          (ii) said distal second section is tapered at a second angle, shallower than said first angle, toward the center of said core of said distal section from said second radius having the third V-number equal to the first V-number.

12. The optical fiber of claim 10 wherein said proximal first section has a first longitudinal length and said distal second section has a second longitudinal length.

13. The optical fiber of claim 12 wherein said first longitudinal length is between about 0.1%–30% of said second longitudinal length.

14. The optical fiber of claim 12 wherein said first longitudinal length is between about 1%–20% of said second longitudinal length.

15. The optical fiber of claim 12 wherein said first longitudinal length is between about 2%–15% of said second longitudinal length.

16. The optical fiber of claim 12 wherein said first longitudinal length is between about 5%–12% of said second longitudinal length.

17. The optical fiber of claim 11 wherein said first angle is between about 0.01–30 degrees.

18. The optical fiber of claim 11 wherein said first angle is between about 0.05–15 degrees.

19. The optical fiber of claim 11 wherein said first angle is between about 0.1–10 degrees.

20. The optical fiber of claim 11 wherein said first angle is between about 0.2–5 degrees.

* * * * *